United States Patent [19]

Carney et al.

[11] Patent Number: 4,950,678
[45] Date of Patent: Aug. 21, 1990

[54] SUBSTITUTED N-(HETEROCYCLIC-SUBSTITUTED PHENYL)-N'-BENZYLUREAS

[75] Inventors: Robert L. Carney, Palo Alto; John M. Gruber, Menlo Park; Alfred S. T. Lui, Redwood City, all of Calif.

[73] Assignee: Sandoz Ltd., Basel, Switzerland

[21] Appl. No.: 386,333

[22] Filed: Jul. 27, 1989

Related U.S. Application Data

[63] Continuation-in-part of Ser. No. 187,164, Apr. 28, 1989, which is a continuation-in-part of Ser. No. 12,577, Feb. 9, 1987, abandoned, which is a continuation-in-part of Ser. No. 840,814, Mar. 18, 1986, abandoned.

[51] Int. Cl.$^5$ ............... A01N 43/50; A01N 43/56; C07D 231/56; C07D 231/38
[52] U.S. Cl. .................. 514/340; 546/271; 546/273; 546/276; 546/278; 546/279; 548/225; 548/261; 548/255; 548/336; 548/346; 548/327; 548/329; 548/325; 548/341; 548/379; 548/372; 548/561; 548/563; 548/369; 548/323; 548/337; 548/375

[58] Field of Search .............. 546/271, 273, 276, 278, 546/279; 548/225, 261, 255, 336, 337, 346, 327, 329, 325, 341, 379, 372, 561, 563, 369, 323, 337, 375; 514/340, 341, 343, 359, 397, 398, 399, 406, 407, 422, 423, 424, 425, 427

[56] References Cited

U.S. PATENT DOCUMENTS 3,748,356 7/1973 Wellinga et al. .................. 260/553
4,847,258 7/1989 Sturm et al. ...................... 514/274

FOREIGN PATENT DOCUMENTS 3732541 4/1989 Fed. Rep. of Germany ........ 231/12
WO86/03941 7/1986 PCT Int'l Appl. .................... 47/34

OTHER PUBLICATIONS

Nakagawa et al., Pesticide Biochem. & Physiol. 21, 309–324 (1984).

*Primary Examiner*—Mary C. Lee
*Assistant Examiner*—Joseph K. McKane
*Attorney, Agent, or Firm*—Allen E. Norris

[57] ABSTRACT

Novel substituted N-(heterocyclic-substituted phenyl)-N'-benzoyl-ureas, processed for producing these compounds, intermediates therefor, compositions thereof and the use of the compounds for the control of pests.

19 Claims, No Drawings

SUBSTITUTED N-(HETEROCYCLIC-SUBSTITUTED PHENYL)-N'-BENZYLUREAS

This is a continuation-in-part of Ser. No. 187,164 filed Apr. 28, 1988, which is a continuation-in-part of Ser. No. 012,577, filed on Feb. 9, 1987, now abandoned, which is a continuation-in-part of Ser. No. 840,814, filed on Mar. 18, 1986, now abandoned.

The present invention relates to substituted N-(heterocyclic-substituted phenyl)-N'-benzoylureas, to processes for producing these compounds, to intermediates therefor, to compositions thereof and to the user of the compounds for the control of pests, and in particular for the control of insects and acarids.

More particularly, the compounds of the present invention are represented by the following formula (A):

(A)

wherein, each of $X^1$, $X^2$, $X^3$ and $X^5$ is independently hydrogen, halogen, $C_{1-18}$alkyl or $C_{1-8}$alkoxy;

$X^4$ is hydrogen, halogen, unsubstituted or halogenated $C_{1-8}$alkyl- or COOR.

$X^6$ is hydrogen, halogen, $C_{1-8}$alkyl or COOR';

Y is oxygen or sulfur;

A is nitrogen or C—$R^3$;

each of R, R' R" is hydrogen of $C_{1-8}$alkyl;

each of $R^1$ and $R^4$ is independently hydrogen; halogen; halogenated $C_{1-8}$alkyl; unsubstituted or halogenated $C_{1-8}$alkoxy; unsubstituted or halogenated $C_{1-8}$alkylthio; or Q, Q—O— or Q—S—, unsubstituted or substituted with 1 to 4 halogen atoms or with a $C_{1-4}$alkyl, $C_{1-4}$alkoxy or trifluoromethyl group and 0 to 3 halogen atoms;

Q is an aromatic ring system; and each of $R^2$ $R^3$ is independently hydrogen; halogen; cyano; unsubstituted or halogenated $C_{1-8}$alkyl; unsubstituted or halogenated $C_{1-8}$alkoxy; unsubstituted or halogenated $C_{1-8}$alkylthio; COOR"; Q, Q—O— or Q—S—unsubstituted or substituted with 1 to 4 halogen atoms or with a $C_{1-4}$alkyl, $C_{1-4}$alkoxy or trifluoromethyl group and 0 to 3 halogen atoms; or either $R^1$ and $R^2$ or $R^2$ and $R^3$ can together form a bridging group of 4 carbon atoms, saturated or unsaturated, and optionally substituted with 1 to 4 halogen atoms or with a trifluoromethyl group and 0 to 3 halogen atoms;

with the proviso that where A is C—$R^4$ and B is C—$R^3$, not all of $R^1$, $R^2$, $R^3$ and $R^4$ may be hydrogen; and the agriculturally acceptable salts or metal complexes thereof.

In the description hereinafter and the appended claims, each of A, B, R-$R^4$, $X^1$-$X^6$ and Y is as defined above, unless otherwise specified.

In the practice of the present invention, Y is preferably oxygen.

A is preferably nitrogen.

B is preferably C—$R^3$.

Where any of the substituents $X^1$-$X^6$ and $R^1$-$R^4$ is or comprises halogen, such halogen is conveniently selected from bromo, chloro and fluoro.

Where any of $X^1$-$X^6$ is $C_{1-8}$alkyl, it is preferably of one to four carbons and is more preferably of one or two carbons.

Where any of $X^1$-$X^3$ and $X^5$ is $C_{1-8}$alkoxy, it is preferably of one to four carbons and is more preferably of one or two carbons.

Where any of R, R' and R" is $C_{1-8}$alkyl, it is preferably of one to four carbons and is more preferably of one or two carbons.

The terms halogenated $C_{1-8}$alkyl, halogenated $C_{1-8}$alkoxy and halogenated $C_{1-8}$alkylthio refer to $C_{1-8}$alkyl, $C_{1-8}$alkoxy and $C_{1-8}$alkylthio, respectively, substituted by one to six, preferably one to three halogens; such halogen is preferably chloro or fluoro.

Q refers to an aromatic ring system such as phenyl, pyridyl, thienyl and naphthyl, preferably phenyl. Where the aromatic aryl is substituted, it may bear from one to four, preferably one or two substituents. Thus the aromatic ring, is preferably substituted with one methyl, methoxy or $CF_3$ group and zero or one halogen atoms, or with one to three halogens, more preferably one or two halogens. Particularly preferred substituted aromatic significances are halophenyl, dihalophenyl, methylphenyl and trifuloromethylphenyl.

The term agriculturally acceptable salts or metal complexes of the aryl ureas refers to ammonium, sulfonium, phosphonium or metal ions such as, for example, tetraethylammonium, benzyltrimethylammonium, trimethylsulfonium, trimethylsulfoxonium, ethyltriphenylphosphonium, titanium(IV), zirconium(IV) or ZINC(II).

X' is preferably hydrogen or halogen, more preferably hydrogen, chloro or fluoro.

$X^2$ is preferably hydrogen of halogen; such halogen is preferably fluoro.

$X^3$ is preferably hydrogen or halogen, more preferably hydrogen.

$X^4$ conveniently signifies hydrogen, halogen, $C_{1-4}$alkyl, $CF_3$ or COOR; it is preferably hydrogen, chloro, methyl or $CF_3$.

$X^5$ is preferably hydrogen, $C_{1-4}$alkyl or halogen; it is more preferably hydrogen, chloro or methyl.

$X^6$ is preferably hydrogen or halogen, more preferably hydrogen, chloro or fluoro especially hydrogen or fluoro.

$R^1$ conveniently signifies hydrogen, halogen, $CF_3$, $C_{1-14}$alkoxy, unsubstituted or substituted aryl, or together with $R^2$ forms a bridging group of 4 carbon atoms. $R^1$ is preferably hydrogen, bromo, chloro, $CF_3$ or unsubstituted or substituted phenyl, more preferably hydrogen or chloro.

$R^2$ conveniently signifies hydrogen, halogen, $C_{1-4}$alkyl, $CF_3$COOR', cyano, unsubstituted or substituted phenyl, or together with either $R^1$ or $R^3$ forms a bridging group of 4 carbon atoms. $R^2$ is preferably hydrogen bromo, chloro, $CF_3$, or mono- or disubstituted phenyl. $R^2$ is more preferably hydrogen, bromo or chloro.

$R^3$ conveniently signified hydrogen, halogen, $CF_3$, $C_{1-4}$alkyl, unsubstituted or substituted phenyl, or together with $R^2$ forms a bridging group of 4 carbon atoms. $R^3$ is preferably hydrogen, bromo, chloro, $CF_3$, or mono- or disubstituted phenyl. $R^3$ is more preferably hydrogen, bromo, chloro, $CF_3$, 4-bromophenyl or 4-chlorophenyl.

Where $R^1$ and $R^2$ together form a bridging group, this is preferably of the formula CH=CH—CH=CH. Such group is preferably unsubstituted or substituted by one or two halogen atoms; such halogen is preferably chloro.

Where $R^2$ and $R^3$ together form a bridging group, this is preferably of the formula $(CH_2)_4$.

The compounds of the present invention of formula A are new substances which can be prepared by methods known in the art, such as those described in U.S. Pat. Nos. 3,748,356 and 3,933,908 and in U.K. Application GB 2134518, for example. More particularly, they can be obtained by (a) reacting a compound of formula (I)

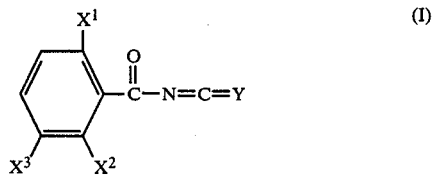

wherein $X^1$, $X^2$, $X^3$ and Y are as defined above, with a compound of formula (II) t,51

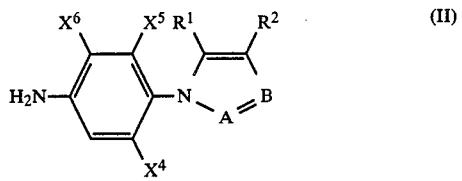

wherein $X^4$, $X^5$, $X^6$, $R^1$, $R^2$, A and B are as defined above; or (b) by reacting a benxamide of formula (III)

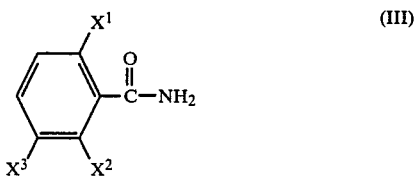

wherein $X^1$, $X^2$ and $X^3$ are as defined above, with a compound of formula (IV)

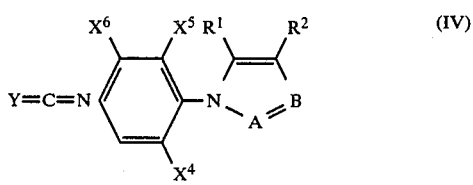

wherein Y, $R^1$, $R^2$, $X^4$, $X^5$, $X^6$, A and B are as defined above.

The reaction of compounds of formula I with compounds of formula II (process a) may be effected under the conditions known for the preparation of N-benzoyl-N'-phenylureas from the corresponding benzoyl isocyanates and anilines.

The reaction is conveniently carried out in a solvent which is inert under the reaction conditions, e.g. methylene chloride, toluene or dimethylformamide. A suitable reaction temperature may vary from −10° C. to the boiling point of the solvent used, and preferably is about room temperature or moderately above or below room temperature, e.g. between 15° and 40° C.

The reaction of compounds of formula III with compounds of formula IV (process b) may be effected under the conditions known for the preparation of N-benzoyl-N'-phenylureas from the corresponding benzamides and phenylisocyanates.

The reaction is conveniently carried out in a solvent which is inert under the reaction conditions and at a reaction temperature of between 0° and 120° C., preferably at the boiling point of the solvent used, and optionally in the presence of an organic base, such as pyridine.

The salts of the compounds of formula A may be prepared by reaction of the ammonium, sulfonium or phosphonium halide with the compound A in the presence of a base, such as potassium hydroxide, and a water-immiscible solvent, such as dichloromethane.

The metal complexes of the compounds of formula A may be prepared by reaction of the compound A with the metal alkoxide, such as titanium tetraisopropoxide, under vacuum at temperature that permits removal of the alcohol product by distillation, typically 75° to 100°.

The compounds of formula (A) may be recovered from the reaction mixture in which they are formed by working up by established procedures.

The starting materials and reagents employed in the process described herein are either known or, insofar as they are not know, may be produced in a manner analogous to the processes described herein to known processes.

The compounds of the present invention of formula A are useful pest control agents, particularly for the control of insects, mites, ticks and helminths. These compounds can be effective control agents for insects of, for example, the orders Leipdoptera, Hemiptera, Homoptera, Coleoptera, Diptera, Orthoptera and Siphonaptera, and other insects, as well as for mites and ticks of the class Acari, including mites of the families Tetranychidae and Tarsonemidae and ticks of the families Argasidae and Ixodidae. The compounds can be applied to the pest of its locus in a pest-controlling amount, usually of the order of 0.001 μg to 10 μg, especially 0.001 μg to 1 μg per insect, mite or tick, depending on the mode and conditions of application as well as on the pest involved.

These compounds may be useful anthelminthic agents against parasites of warm-blooded animals and of plants, such as, for example, intestinal and extraintestinal nematodes of the families Ascaridae and Trichostrongylidae and plant parasitic nematodes of the families Heteroderidae and Tylenchidae.

Additionally, compounds of formula A may posses a repellent and/or antifeedant action on terrestrial snails and slugs. The compounds may be useful for control of arthropod endoparasites and ectoparasites of vertebrates, either by topical application or by oral administration to the host animal.

The compounds of the present invention may be used as an active ingredient in anti-fouling marine paints to prevent attachment of marine arthropods, such as barnacles.

In the use of the compounds of formula A for combating pests, a compound of formula A, or mixtures thereof, can conveniently be employed as pesticidal compositions in association with acceptable diluent(s) for application to the pest or its locus. Such compositions also form part of the present invention.

Suitable formulations contain from 0.01 to 99% by weight of active ingredient, from 0 to 20% of surfactant and from 1 to 99.99% of solid or liquid diluent(s). Higher rations of surfactant to active ingredient are sometimes desirable and are achieved by incorporation into the formulation or by tank mixing. Application forms of a composition generally contain between 0.01 and 25% by weight of active ingredient. Lower or higher levels of active ingredient can, of course, be present depending on the intended use, the physical properties of the compound and the mode of application. Concentrate forms of a composition intended to be diluted before use generally contain between 2 and 90%, preferably between 5 and 81% by weight of active ingredient.

Useful formulations of the compounds of formula A include dusts, granules, suspension concentrates, wettable powders, emulsifiable concentrates, flowables and the lie, most preferably emulsifiable concentrates. They are obtained by conventional manner, e.g. by mixing a compound of formula A with the diluent(s) and optionally with other ingredients.

Alternatively, the compounds of formula A may be used in microencapsulated form.

The compounds of formula A can be combined with a cyclodextrin to make a cyclodextrin inclusion complex for application to the pest or its locus.

Agriculturally acceptable additives may be employed in the pesticidal compositions to improve the performance of the active ingredient and to reduce foaming, caking and corrosion, or to improve solubility or retard crystallization, for example.

"Surfactant" as used herein means an agriculturally acceptable material which imparts emulsifiability, spreading, wetting dispersibility or other surface-modifying properties. Examples of surfacants are sodium lignin sulfonate and lauryl sulfate.

"Diluent" as used herein means a liquid of solid agriculturally acceptable material used to dilute a concentrated material to a usable or desirable strength. For dusts or granules it can be e.g. talc, kaolin or diatomaceous earth, for liquid concentrate forms for example a hydrocarbon such as xylene or an alcohol such as isopropanol, and for liquid application forms i.e. water or diesel oil.

The compositions of this invention can also comprise other compounds having biological activity, e.g. compounds having similar or complementary pesticidal or insect growth regulating activity or compounds having antidotal, fungicidal, herbicidal or insect attractant activity.

The following examples are provided to illustrate the practice of the present invention. Temperature is given in degrees Centigrade. RT means room temperature. Parts and percentages are by weight. The symbols *, # and + when used in connection with melting points means "gas", "softens" and "decomposes" respectively.

COMPOSITION EXAMPLES

Example A

| Dust | |
|---|---|
| Compound 106 | 5.1% |
| kaolin | 94.9 |

Example B

| Flowable | |
|---|---|
| Compound 106 | 48.0% |
| Darvon No. 1 (dispersant) | 4.0 |
| Veegum (thickener) | 0.4 |
| Surfynol TGE (antifoam) | 0.1 |
| water | 41.3 |
| propylene glycol (antifreeze) | 6.0 |
| Kelzan ® (thickener) | 0.2 |

Darvan is sodium naphthalene sulfonic acid formaldehyde.
Veegum is colloidal magnesium aluminum silicate.
Surfynol is acetylenic diol blend.
Kelzan is xanthan gum.

Example C

| Wettable Powder | |
|---|---|
| Compound 106 | 81.0% |
| kaolin | 14.8 |
| Marasperse ® N-22 (dispersant) | 4.0 |
| Aerosol ® OTB (wetting agent) | 0.2 |

Marasperse is sodium lignin sulfonate.
Aerosol is dioctyl ester of sodium sulfosuccinic acid.

Example D

| Emulsifiable Concentrate | |
|---|---|
| Compound 106 | 5% |
| 1-n-octyl-2-pyrrolidinone | 55 |
| 1-methyl-2-pyrrolidinone | 10 |
| TENECO ® 500–100 (solvent mix) | 25 |
| TOXIMUL ® (surfactant) | 5 |

TENNECO ® 500–100 is a mixture of trimethyl benzene and xylene.
TOXIMUL ® HHF is an anionic- nonionic surfactant blend.

From the point of view of ease of application and efficacy, Emulsifiable Concentrates are preferred.

PREPARATION OF FINAL UREAS

Example 1

N-4-(4-chloro-1-pyrazolyl(phenyl-N'-2,6-difluorobenzoylurea 2,6-Difluorobenzoyl isocyanate (0.47 g, 2.6 mmol) is added dropwise to a solution of 4-(4chloro-1-pyrazolyl)aniline (0.50 g, 2.6 mmol) in 8 ml of methylene chloride. The mixture is stirred for 30 min., then diluted with methylene chloride and filtered. The solid is washed with ether and fired to give N-4-(4-chloro-1-pyrazolyl)phenyl-N'-2,6-difluorobenzoylurea (compound 1 under Table A).

Example 2

N-3,5-dichloro-4-(1-pyrazolyl)phenyl-N'-2,6-difluorobenzoylurea

To a solution of 3,5-dichloro-4-(1-pyrazolyl)aniline (0.17 g, 0.75 mmol) in 7 ml of methylene chloride and 1 ml of DMF is added 2,6-difluorobenzoyl isocyanate (0.14 g, 0.75 mmol). The resulting mixture is stirred for 5 min., then diluted with ethyl acetate, washed with water and with brine, and dried. After the solvent is evaporated off, ether is added to the solid residue, the suspension is filtered and the solid is washed with ether and dried to give N-3,5-dichloro-4-(1-pyrazolyl)phenyl-N'-2,6-difluorobenzoylurea (compound 2 under Table A).

nmr (d₆-DMSO) 6.50 (m, 1H), 7.22 (m, 2H), 7.58 m, 1H), 7.76 (m, 1H), 7.96 (s, 2, 2H) and 7.98 ppm (m, 1H).

Example 3

Following generally the procedures of Example 1 or 2, each of the final product ureas under Table A and B and those listed under column I below is prepared from the corresponding aniline and benzoyl isocyanate or benzoyl isothiocyanate intermediates.

I

128. N-3,5-dichloro-4-(2-indazoplyl)phenyl-N'-2,6-difluorobenzoyl urea, m.p. 209°–210°;
129. N-3,5-dichloro-4-(2-indazoyl)phenyl-N'-2-chlorobenzoyl urea, m.p. 216°–217°;
130. N-3,5-dichloro-4-(4,5,6,7-tetrahydroisoindol-2yl)-phenyl-N'-2,6-difluorobenzoylurea, m.p. 240°–242°;
131. N-3,5-dichloro-4-(2,5-dichloro-1-pyrrolyl)phenyl-N'-2,6-difluorobenzoylurea, m.p. 206°–208°;
132. N-3,5-dichloro-4-(2,3,4,5-tetrachloro-1-pyrrolyl)-phenyl-N'-2,6difluorobenzoylurea, m.p. 244°–245°;
133. N-3,5-dichloro-4-(3,4-dichloro-1-pyrrolyl)phenyl-N'-2,6-difluorobenzoylurea, m.p. 236°–239°;
134. N-3,5-dichloro-4-[3-chloro-4-(2,4-dichlorophenyl)-1-pyrrolyl]-phenyl-N'-2,6-difluorobenzoylurea, m.p. 200–206°;
135. N-3,5dichloro-4-(4,5,6,7-tetrahydroisoindol-2yl)-phenyl-N'-2-chlorobenzoylurea, m.p. 230–231°;
136. N-3,5-dichloro-4- (2,5-dichloro-1-pyrrolyl)phenyl-N'-2chlorobenzoylurea;
137. N-3,5-dichloaor-4-(2,3,4,5-tetrachloro-1-pyrrolyl)-phenyl-N'-2-chlorobenzoylurea, m.p. 234–235°;
138. N-3,5- dichloro-4(3,4-dichloro-1pyrrp;y;)phenyl-N'-2-chlorobenzolyurea, m.p. 220–221°;
139. N-3,5-dichloro-4-[3-chloro-4-(2,4- dichlorophenyl)-1-pyrrolyl]-phenyl-N'-2chlorobenzoylurea, m.p. 177–181; °;
140. N-3,5-dichloro-4-(4,5,6,7-tetrahydroisoindol-2-yl)phenyl-N'-2-chloro-5-fluorobenzoylurea;
141. N-3,5-dichloro-4-[3,4bis(trifluoromethyl)-1-pyrazolyl]-phenyl-N'-2-chloro-5-fluorobenzoylurea;
142. N-3,5-dichloro-4-(4,5-dichloro-1-benzotriazolyl)-phenyl-N'-2-chloro-5-fluorobenzoylurea;
143. N-3,5-dichloro-4-(4,5,6,7-tetrahydroisoindol-2-yl)phenyl-N'-2-chlorobenzoylthiourea;
144. N-3,5-dichloro-4-(3,4-dochloro-1pyrrolyl)phenyl-N'-2chlorobenzoylthiourea.
145. N-3,5-dichloro-4-[3,4-bis(trifluoromethyl)-1-pyrazolyl]phenyl-N'-2-chlorobenzoylthiourea;
146. N-3,5-dichloro-4-[4-chloro-3-(4chlorophenyl)-1-pyrazolyl]-phenyl-N'-2-chlorobenzoylthiourea;
147. N-3,5-dichloro-4-(4,5-dichloro-1-benzotriazolyl)-phenyl-N'-2-chlorobenzoylthiourea;
148. N-3,5-dichloro-4-[4chloro-3-(4-chlorophenyl)-1-pyrazoly]-phenyl-N'-2,6-difluorobenzoylurea, m.p. 166–167.5°.

BIOLOGICAL ACTIVITY

EXAMPLE 4

Early (0–24 hr) third instar larvae of the tobacco budworm *Heliothis virescesn*, are topically treated on the dorsal abdomen with 1 ul of acetone dilution of the test compound at the concentration to be tested. The treated larvae are placed on artificial diet in individual cells of a plastic grid contained in a covered plastic petri dish. The containers are held at 27° C., 16 hour photoperiod until all larvae are either dead or have molted to fifth instar larvae. The compounds of formula A demonstrated insecticidal activity.

EXAMPLE 5

Mature third instar larvae (wandering stage having left food) of the housefly, *Musca domestica*, are topically treated with 1 ul of acetone dilution of the test compound at the concentration to be tested. The treated larvae are allowed to pupate and are held at 31° C., 16 hour photoperiod until all insects have died or emerged from pupae to adults (about 7 days). The compound of formula A demonstrated insecticidal activity.

EXAMPLE 6

Early (0–24 hr) third instar larvae of the beet armyworm, *Spodoptera exigua*, are topically treated on the dorsal abdomen with 1 ul of acetone dilution of the test compound at the concentration to be tested. The treated larvae are placed on artificial diet in a covered plastic petri dish. The containers are held at 27° C., 16 hour photoperiod until all larvae are either dead or have pupated. The compounds of formula A demonstrated insecticidal activity.

TABLE A

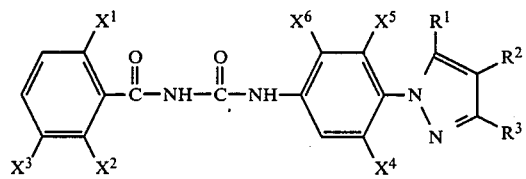

| Cpd | $X^1$ | $X^2$ | $X^3$ | $X^4$ | $X^5$ | $X^6$ | $R^1$ | $R^2$ | $R^3$ | m.p. (°C.) |
|---|---|---|---|---|---|---|---|---|---|---|
| 1 | F | F | H | H | H | H | H | Cl | H | 240–242 |
| 2 | F | F | H | Cl | Cl | H | H | H | H | 211–212 |
| 3 | F | F | H | Cl | Cl | H | H | Cl | H | 229–230 |
| 4 | F | F | H | Cl | Cl | H | H | Br | H | 233–235 |
| 5 | F | F | H | Cl | Cl | H | H | CF₃ | CF₃ | 220–223 |
| 6 | F | F | H | Cl | Cl | H | H | H | Cl | 217–219 |
| 7 | F | F | H | Cl | Cl | H | H | Br | Br | 224–227 |

TABLE A-continued

[Structure: X¹,X²,X³ substituted benzoyl-NH-C(O)-NH-phenyl (with X⁴,X⁵,X⁶) -N-pyrazole(R¹,R²,R³)]

| Cpd | X¹ | X² | X³ | X⁴ | X⁵ | X⁶ | R¹ | R² | R³ | m.p. (°C.) |
|---|---|---|---|---|---|---|---|---|---|---|
| 8 | F | F | H | Cl | Cl | H | H | H | 4-Cl-C₆H₄ | 210–212 |
| 9 | F | F | H | Cl | Cl | H | H | 4-Cl-C₆H₄ | H | 246–247 |
| 10 | F | F | H | Cl | Cl | H | H | H | CF₃ | 202.5–203.5 |
| 11 | F | F | H | Cl | Cl | H | H | CF₃ | H | 222–223 |
| 12 | F | F | H | Cl | Cl | H | Cl | H | CF₃ | 206–207 |
| 13 | F | F | H | Cl | Cl | H | H | H | C(CH₃)₃ | 204–205 |
| 14 | F | F | H | Cl | Cl | H | H | Cl | 4-Cl-C₆H₄ | 206.5–208.5 |
| 15 | F | F | H | Cl | Cl | H | H | Cl | Cl | 231–233 |
| 16 | F | F | H | Cl | Cl | H | H | Cl | CF₃ | 222.5–224 |
| 17 | F | F | H | Cl | Cl | H | Cl | Cl | CF₃ | 203–204 |
| 18 | F | F | H | Cl | Cl | H | CF₃ | H | CF₃ | 212.5–214 |
| 19 | F | F | H | H | H | H | CF₃ | H | CF₃ | 211.5–212 |
| 20 | F | F | H | H | H | H | Cl | H | CF₃ | 197–199 |
| 21 | F | F | H | H | Cl | H | H | Cl | H | 230–231 |
| 35 | F | F | H | Cl | H | H | H | Cl | 4-Cl-C₆H₄ | |
| 36 | F | F | H | CF₃ | H | H | H | Cl | 4-Cl-C₆H₄ | 242–244 |
| 37 | F | F | H | CF₃ | H | H | Cl | H | CF₃ | 192.5–195 |
| 38 | F | F | H | Cl | Cl | H | Cl | Cl | Cl | 236–238 |
| 39 | F | F | H | Cl | Cl | H | H | Br | 4-Cl-C₆H₄ | 204–206 |
| 40 | F | F | H | Cl | Cl | H | Br | Br | Br | 249–250 |
| 41 | F | F | H | Cl | Cl | H | CF₃ | H | Cl | 209–211 |
| 42 | F | F | H | H | H | F | H | H | Cl, 4-Cl-C₆H₄ | 121.5–122.5 |
| 43 | F | F | H | Cl | H | F | H | Cl | 4-Cl-C₆H₄ | 238–240 |

TABLE A-continued

[Structure: X¹,X²,X³-substituted benzoyl urea linked to X⁴,X⁵,X⁶-substituted phenyl bearing a pyrazole with R¹, R², R³ substituents]

| Cpd | X¹ | X² | X³ | X⁴ | X⁵ | X⁶ | R¹ | R² | R³ | m.p. (°C.) |
|---|---|---|---|---|---|---|---|---|---|---|
| 44 | F | F | H | CH₃ | H | H | H | Cl | 4-Cl-phenyl | 236–238 |
| 45 | F | F | H | Cl | H | CH₃ | H | Cl | 4-Cl-phenyl | 208–210 |
| 46 | F | F | H | Cl | Cl | H | H | 2,4-diCl-phenyl | H | 232–234 |
| 47 | F | F | H | Cl | Cl | H | H | 4-Br-phenyl | H | 253–254 |
| 48 | F | F | H | CH₃ | CH₃ | H | H | Cl | 4-Cl-phenyl | 217–219 |
| 49 | F | F | H | Cl | Cl | H | OCH₃ | Cl | 4-Cl-phenyl | 216–217 |
| 50 | F | F | H | Cl | Cl | H | H | C(O)OCH₂CH₃ | H | 213–215 |
| 51 | F | F | H | C(O)OCH₃ | H | H | H | Cl | 4-Cl-phenyl | 210–212 |
| 52 | F | F | H | Cl | H | H | Cl | H | CF₃ | 207.5–208.5 |
| 53 | F | F | H | Cl | H | H | H | Br | H | 226–228 |
| 54 | F | F | H | CF₃ | H | H | H | Br | H | 206–208 |
| 55 | F | F | H | Cl | Cl | H | H | H | 2-Cl-phenyl | 230–232 |
| 56 | F | F | H | Cl | Cl | H | H | H | 2,4-diCl-phenyl | 231–232 |
| 57 | F | F | H | Cl | Cl | H | H | H | 2,3-diCl-phenyl | 224–225 |

TABLE A-continued
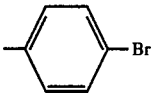
| Cpd | X¹ | X² | X³ | X⁴ | X⁵ | X⁶ | R¹ | R² | R³ | m.p. (°C.) |
|-----|----|----|----|----|----|----|----|----|----|-----------|
| 58 | F | F | H | Cl | Cl | H | H | H | 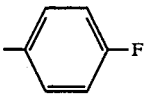 4-Br-phenyl | 224–225 |
| 59 | F | F | H | Cl | Cl | H | H | H | 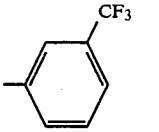 4-F-phenyl | 222–224 |
| 60 | F | F | H | Cl | Cl | H | H | H | 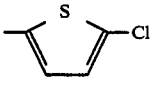 3-CF₃-phenyl | 199–200 |
| 61 | F | F | H | Cl | Cl | H | H | H | 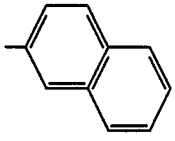 5-Cl-thienyl | 226–228 |
| 62 | F | F | H | Cl | Cl | H | H | H |  naphthyl | 228–229 |
| 63 | F | F | H | Cl | Cl | H | H | CN | H | 246–248 |
| 64 | F | H | H | Cl | Cl | H | Cl | Cl | CF₃ | 193–194.5 |
| 65 | F | H | H | Cl | Cl | H | H | Cl | 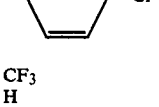 4-Cl-phenyl | 198–200 |
| 66 | F | H | H | Cl | H | H | Cl | H | CF₃ | 202–203 |
| 67 | F | H | H | Cl | H | H | H | Br | H | 213–215 |
| 68 | F | H | H | CF₃ | H | H | H | Br | H | 170–172 |
| 69 | F | H | H | Cl | Cl | H | H | H | 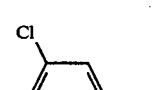 2,4-diCl-phenyl | 215–216 |
| 70 | F | H | H | Cl | Cl | H | H | H | 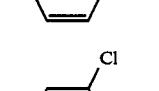 3,4-diCl-phenyl | 234–236 |
| 71 | F | H | H | Cl | Cl | H | H | H | 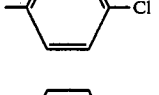 4-Br-phenyl | 218–219 |
| 72 | F | H | H | Cl | Cl | H | H | H |  4-F-phenyl | 199–201 |

TABLE A-continued

| Cpd | X¹ | X² | X³ | X⁴ | X⁵ | X⁶ | R¹ | R² | R³ | m.p. (°C.) |
|---|---|---|---|---|---|---|---|---|---|---|
| 73 | F | H | H | Cl | Cl | H | H | H | 3-CF₃-phenyl | 202–204 |
| 74 | CH₃ | H | H | Cl | Cl | H | Cl | Cl | CF₃ | 211–212.5 |
| 75 | CH₃ | H | H | Cl | Cl | H | H | Cl | 4-Cl-phenyl | 243–245 |
| 76 | Cl | H | F | Cl | Cl | H | Cl | Cl | CF₃ | 211–212.5 |
| 77 | Cl | F | H | Cl | Cl | H | Cl | Cl | CF₃ | 220.5–222 |
| 78 | Cl | Cl | H | Cl | Cl | H | Cl | Cl | CF₃ | 231.5–232.5 |
| 79 | Cl | H | H | H | H | H | H | Cl | H | |
| 80 | Cl | H | H | Cl | Cl | H | H | H | H | 200–202 |
| 81 | Cl | H | H | Cl | Cl | H | H | Cl | H | 236–238 |
| 82 | Cl | H | H | Cl | Cl | H | H | Br | H | 234–236 |
| 83 | Cl | H | H | Cl | Cl | H | H | CF₃ | CF₃ | 195–196 |
| 84 | Cl | -H | H | Cl | Cl | H | H | H | Cl | 202–203 |
| 85 | Cl | H | H | Cl | Cl | H | H | Br | Br | 208–210 |
| 86 | Cl | H | H | Cl | Cl | H | H | H | 4-Cl-phenyl | 201.5–203 |
| 87 | Cl | H | H | Cl | Cl | H | H | 4-Cl-phenyl | H | 227–230 |
| 88 | Cl | H | H | Cl | Cl | H | H | H | CF₃ | |
| 89 | Cl | H | H | Cl | Cl | H | H | CF₃ | H | 207–208 |
| 90 | Cl | H | H | Cl | Cl | H | Cl | H | CF₃ | 209–210 |
| 91 | Cl | H | H | Cl | Cl | H | H | H | C(CH₃)₃ | 200–201 |
| 92 | Cl | H | H | Cl | Cl | H | H | Cl | 4-Cl-phenyl | 229–231.5 |
| 93 | Cl | H | H | Cl | Cl | H | H | Cl | Cl | 220–227 |
| 94 | Cl | H | H | Cl | Cl | H | H | Cl | CF₃ | 202–203 |
| 95 | Cl | H | H | Cl | Cl | H | Cl | Cl | CF₃ | 203.5–204.5 |
| 96 | Cl | H | H | Cl | Cl | H | CF₃ | H | CF₃ | 204–205 |
| 97 | Cl | H | H | H | H | H | CF₃ | H | CF₃ | |
| 98 | Cl | H | H | H | H | H | Cl | H | CF₃ | |
| 99 | Cl | H | H | H | Cl | H | H | Cl | H | |
| 100 | Cl | H | H | Cl | H | H | H | Cl | 4-Cl-phenyl | 225–226.5 |
| 101 | Cl | H | H | CF₃ | H | H | H | Cl | 4-Cl-phenyl | 198–199 |
| 102 | Cl | H | H | CF₃ | H | H | Cl | H | CF₃ | 183–185 |

TABLE A-continued
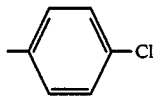
| Cpd | X¹ | X² | X³ | X⁴ | X⁵ | X⁶ | R¹ | R² | R³ | m.p. (°C.) |
|---|---|---|---|---|---|---|---|---|---|---|
| 103 | Cl | H | H | Cl | Cl | H | H | Br | 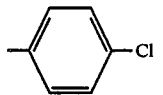 4-Cl-C₆H₄ | 222–224 |
| 104 | Cl | H | H | Cl | Cl | H | Br | Br | Br | 232–233 |
| 105 | Cl | H | H | Cl | Cl | H | CF₃ | H | Cl | 208–209 |
| 106 | Cl | H | H | Cl | Cl | H | Cl | Cl | Cl | 222–224 |
| 107 | Cl | H | H | CH₃ | CH₃ | H | H | Cl | 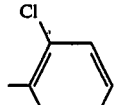 4-Cl-C₆H₄ | 216–218 |
| 108 | Cl | H | H | Cl | H | H | H | Br | H | 243–245 |
| 109 | Cl | H | H | CF₃ | H | H | H | Br | H | 184–186 |
| 110 | Cl | H | H | Cl | Cl | H | H | H | 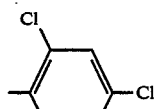 2-Cl-C₆H₄ | 184–187 |
| 111 | Cl | H | H | Cl | Cl | H | H | H | 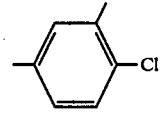 2,4-Cl₂-C₆H₃ | 211–213 |
| 112 | Cl | H | H | Cl | Cl | H | H | H | 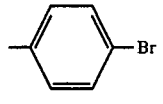 3,4-Cl₂-C₆H₃ | 220–221 |
| 113 | Cl | H | H | Cl | Cl | H | H | H | 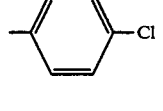 4-Br-C₆H₄ | 210–211 |
| 114 | Cl | H | H | CH₃ | Cl | H | H | Cl | 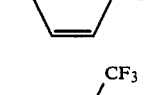 4-Cl-C₆H₄ | 240–242 |
| 115 | Cl | H | H | Cl | Cl | H | H | H | 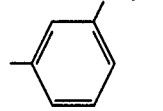 4-F-C₆H₄ | 191–192 |
| 116 | Cl | H | H | Cl | Cl | H | H | H | 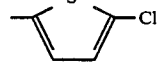 3-CF₃-C₆H₄ | 150–151 |
| 117 | Cl | H | H | Cl | Cl | H | H | H | 5-Cl-thien-2-yl | 220–222 |

TABLE A-continued
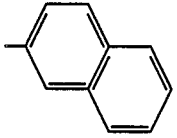
| Cpd | X¹ | X² | X³ | X⁴ | X⁵ | X⁶ | R¹ | R² | R³ | m.p. (°C.) |
|-----|----|----|----|----|----|----|----|----|----|------------|
| 118 | Cl | H | H | Cl | Cl | H | H | H | 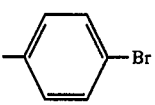 | 228–229 |
| 119 | Cl | H | H | H | Cl | H | Cl | H | CF$_3$ | 209–210 |
| 149 | Cl | H | H | Cl | Cl | H | 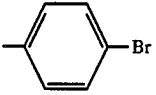 | H | H | 218–220 |
| 150 | Cl | H | H | Cl | Cl | H | 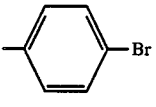 | Cl | H | 225–229 |
| 151 | F | F | H | Cl | Cl | H | 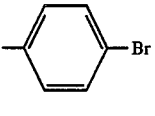 | H | H | 237–238 |
| 152 | F | F | H | Cl | Cl | H | 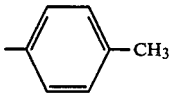 | Cl | H | 301–305 |
| 153 | F | F | H | Cl | Cl | H | H | H | 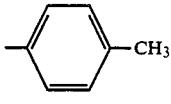 | 198–202 |
| 154 | Cl | H | H | Cl | Cl | H | H | H | 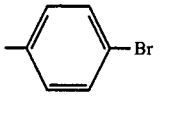 | 205–210 |
| 155 | H | H | H | Cl | Cl | H | H | H | 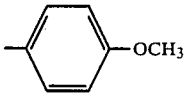 | 256–259 |
| 156 | F | F | H | H | H | H | H | Br | H | 235–237 |
| 157 | F | H | H | H | H | H | H | Br | H | 226–228 |
| 158 | Cl | H | H | H | H | H | H | Br | H | 214–216 |
| 159 | F | F | H | H | H | H | H | Br | F | 238–240 |
| 160 | F | H | H | H | H | H | H | Br | F | 223–225 |
| 161 | Cl | H | H | H | H | H | H | Br | F | 257–259 |
| 162 | F | F | H | Cl | Cl | H | H | Br | 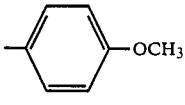 | 209–210 |
| 163 | Cl | H | H | Cl | Cl | H | H | Br | 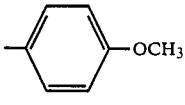 | 210–212 |

TABLE A-continued

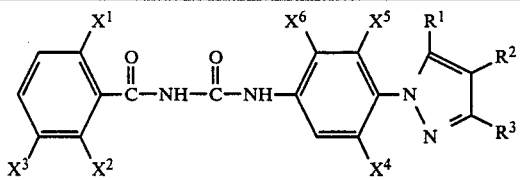

| Cpd | X¹ | X² | X³ | X⁴ | X⁵ | X⁶ | R¹ | R² | R³ | m.p. (°C.) |
|---|---|---|---|---|---|---|---|---|---|---|
| 164 | F | F | H | Cl | Cl | H | H | phenyl | phenyl | 214–243 |
| 165 | Cl | H | H | Cl | Cl | H | H | phenyl | phenyl | 212–214 |
| 166 | F | F | H | Cl | Cl | H | H | 4-Cl-phenyl | 4-Cl-phenyl | 205–209 |
| 167 | Cl | H | H | Cl | Cl | H | H | 4-Cl-phenyl | 4-Cl-phenyl | 160–165 |
| 168 | F | F | H | H | H | H | Cl | Cl | CF₃ | 235–237 |
| 169 | Cl | H | H | H | H | H | Cl | Cl | CF₃ | 193–195 |
| 170 | F | F | H | CF₃ | H | H | Cl | Cl | CF₃ | 219–221 |
| 171 | Cl | H | H | CF₃ | H | H | Cl | Cl | CF₃ | 185–187 |
| 172 | OCH₃ | OCH₃ | H | Cl | Cl | H | H | H | 4-Cl-phenyl | 227–229 |
| 173 | OCH₃ | OCH₃ | H | Cl | Cl | H | H | Br | Br | 228–230 |
| 174 | F | F | H | Cl | Cl | H | H | 4-Cl-phenyl | CF₃ | 204–206 |
| 175 | Cl | H | H | Cl | Cl | H | H | 4-Cl-pyridyl | CF₃ | 208–210 |
| 176 | F | F | H | Cl | H | Cl | Cl | H | CF₃ | 218–220 |
| 177 | Cl | H | H | Cl | H | Cl | Cl | H | CF₃ | 219–220 |
| 178 | Cl | H | H | H | Cl | Cl | Cl | H | CF₃ | 230–231 |
| 179 | F | F | H | H | Cl | Cl | Cl | H | CF₃ | 226–227 |
| 180 | F | F | H | Cl | H | Cl | Cl | Cl | Cl | 224 |
| 181 | F | F | H | H | Cl | Cl | Cl | Cl | Cl | 250–252 |
| 182 | Cl | H | H | Cl | H | Cl | Cl | Cl | Cl | 236–238 |
| 183 | Cl | H | H | H | Cl | Cl | Cl | Cl | Cl | 256–258 |
| 184 | F | F | H | Cl | Cl | F | Cl | Cl | Cl | 233–235 |
| 185 | Cl | H | H | Cl | Cl | F | Cl | Cl | Cl | 224–237 |
| 186 | F | F | H | H | Cl | F | Cl | Cl | Cl | 216–219 |
| 187 | Cl | H | H | H | Cl | F | Cl | Cl | Cl | 203–205 |
| 188 | Cl | H | H | Cl | Cl | Cl | Cl | Cl | Cl | 244–246 |
| 189 | F | F | H | Cl | Cl | Cl | Cl | Cl | Cl | 239–241 |

TABLE B

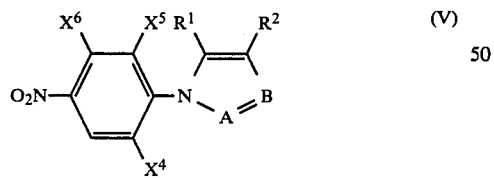

| Cpd | $X^1$ | $X^2$ | $X^4$ | $X^5$ | A | B | $W^1$ | $W^2$ | $W^3$ | m.p. (°C.) |
|---|---|---|---|---|---|---|---|---|---|---|
| 23 | F | F | Cl | Cl | N | CH | H | H | H | |
| 24 | F | F | Cl | Cl | N | C—Cl | H | H | H | 235-237 |
| 25 | F | F | Cl | Cl | N | C—Cl | H | H | Cl | |
| 26 | F | F | Cl | Cl | CH | N | Cl | Cl | H | 225-228 |
| 27 | F | F | Cl | H | CH | N | Cl | Cl | H | |
| 28 | F | F | Cl | Cl | N | N | H | Cl | H | |
| 29 | F | F | Cl | Cl | N | N | Cl | Cl | H | 242-244 |
| 120 | Cl | H | Cl | Cl | N | CH | H | H | H | |
| 121 | Cl | H | Cl | Cl | N | C—Cl | H | H | H | |
| 122 | Cl | H | Cl | Cl | N | C—Cl | H | H | Cl | |
| 123 | Cl | H | Cl | Cl | CH | N | Cl | Cl | H | 246-249 |
| 124 | Cl | H | Cl | H | CH | N | Cl | Cl | H | 225-228 |
| 125 | Cl | H | Cl | Cl | N | N | H | Cl | H | 103-106 |
| 126 | Cl | H | Cl | Cl | N | N | Cl | Cl | H | 222-225 |
| 127 | F | F | H | Cl | C—CF$_3$ | N | Cl | Cl | H | 218-223 |

The starting materials of formulas I, II, III and IV herein are known or, in cases where they are novel, can be produced by methods analogous to known methods or by methods described herein. Thus, the compounds of formula I can be synthesized by methods described in U.S. Pat. No. 3,933,908, for example by (a) treating the corresponding benzamide with oxalyl chloride in the presence of a solvent such as a chlorinated hydrocarbon, as described in *J. Agr. Food Chem.* 21(3):348 (1973); or by (b) reacting the corresponding benzoyl chloride with ammonium thiocyanate.

The aniline derivatives of formula II can be prepared by reduction or catalytic hydrogenation of the corresponding nitro compounds of formula V.

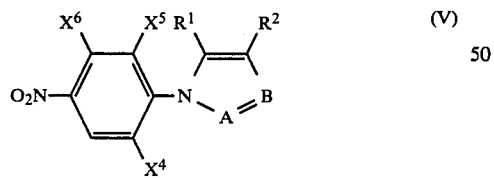

The isocyanates and isothiocyanates of formula IV can be produced by reaction of the aniline derivatives of formula II with phosgene or thiophosgene by use of customary procedures.

The nitro compounds of formula V can be synthesized by reacting a 4-fluoro- or 4-chloronitrobenzene or a 1,4-dinitrobenzene (VI; where Z is fluoro, chloro or nitro) with a substituted pyrrole, pyrozole, imidazole or triazole (VII) or the sodium or potassium salt thereof in a solvent such as tetrahydrofuran, dimethylformanide, hexamethylphosphoramide or N-methylpyrrolidinone.

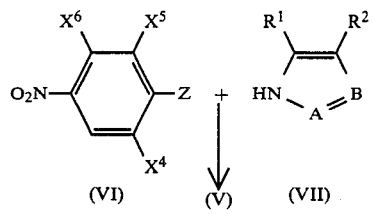

Alternatively, compounds of formula V where $R^2$ is hydrogen, A is nitrogen and B is C—$R^3$ can be prepared by reacting together a 4-nitrophenylhydrazine (VIII) and a beta-diketone (IX) in a solvent such as methanol, with concurrent or subsequent dehydration.

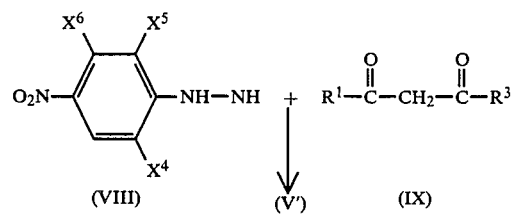

In another method, compounds of formula V where A is nitrogen and B is C—$R^3$ can be prepared by heating a 1(4-nitrophenoxycarbonyl)pyrazole (X) to cause rearrangement and decarboxylation.

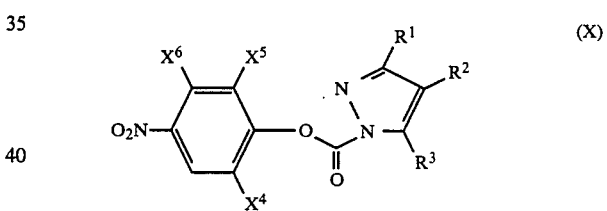

Compounds of formula X can be prepared by reacting together a pyrazole (XI) and a 4-nitrophenyl chloroformate (XII).

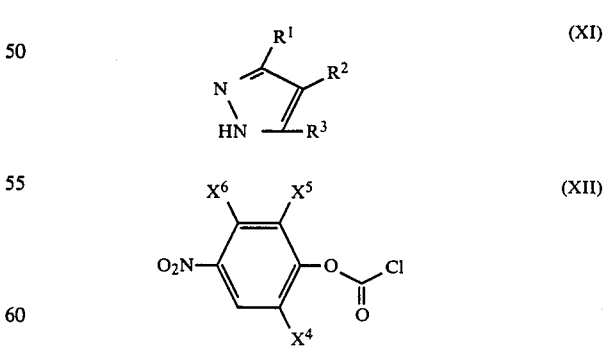

Compounds of formula V where $R^1$ is hydrogen, A is CH and B is C—$R^3$ can be prepared by the following know process (cp. *Org. Synthes,* 47:81–82; 2,5-dialkoxydihydrofuran (XIV); "alk" denoted lower alkyl) are reacted together.

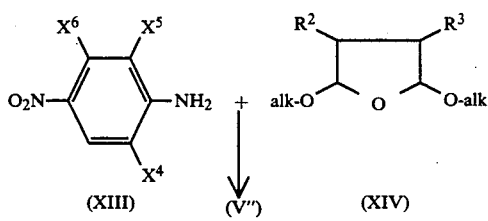

INTERMEDIATE COMPOUNDS

The following examples are presented to illustrate representative methods of preparing the intermediate compounds/

EXAMPLE 3,5-Dichloro-4-fluoronitrobenzene

A mixture of 3,4,5-trichloronitrobenzene (13.55 g, 59 mmol), potassium fluoride (4.65 g, 80 mmol) and dimethylformamide (DMF; 66 ml) is heated at 140° for 15 hours. An additional 2.5 g of potassium fluoride is added and the mixture is stirred an additional 15 hours at 140°. The reaction mixture is poured into water and extracted with ether. The combined organic layers are washed with water and with brine and filtered, and the solvent is removed to give a dark solid, which is purified by column chromatography to give 3,5-dichloro-4-fluoronitrobenzene, a yellow powder.

EXAMPLE 8

4-(4-Chloro-1-pyrazolyl)aniline

Pyrazole (2.0 g, 29 mmol) in tetrahydrofuran (THF) is added dropwise to a suspension of 50% sodium hydride (1.4 g) in THF at RT, followed by stirring at RT for 2 hours. The resulting sodium salt of pyrazole is added to 4-fluoronitrobenzene (4.15 g) in THF at 0°, after which the mixture is heated under reflux for 15 hours. The reaction mixture is poured into saturated aq. ammonium chloride and extracted with ethyl acetate. The combined organic layers are washed with water and with brine and dried to give 1-(4-nitrophenyl)-pyrazole.

A mixture of 1-(4-nitrophenyl)pyrazole (1.0 g, 5.29 mmol) and N-chlorosuccinimide (1.08 g) in 25 ml of chloroform is heated under reflux for ca. 72 hours. The reaction mixture is diluted with chloroform, washed with water and with brine, dried and purified by preparative thin layer chromatography (prep. TLC) to give 4-chloro-1-nitrophenyl)pyrazole.

Iron powder (0.75 g, 13.5 mmol) is added to a mixture of 4-chloro-1-(4-nitrophenyl)pyrazole (0.61 g, 2.7 mmol) and ammonium chloride (1.46 g, 27.0 mmol) in 45 ml ethanol and 16 ml water at 65°–70° over a period of 45 min. The reaction mixture is filtered and the solid is washed with ethyl acetate. Solvent is removed from the filtrate and the residue is taken into ethyl acetate, washed with water and with brine and dried to give 4-(4-chloro-1-pyrazolyl)aniline.

EXAMPLE 9

3,5-Dichloro-4-(1-pyrazolyl)aniline

Pyrazole (1.43 g, 21,0 mmol) in 3 ml of DMF is added dropwise at RT to a suspension of sodium hydride (50%; 1.0 g, 21.0 mmol) in 10 ml of DMF. The mixture is stirred at RT for 30 min., after which it is added dropwise at 5° over a period of 30 min. to a solution of 3,5-dichloro-4-fluoronitrobenzene (3.0 g, 15.0 mmol) in 20 ml of DMF. After reaction is complete, the reaction mixture is quenched with water and extracted with ethyl acetate. The combined organic layers are washed with water and with brine and dried to give a yellow solid, 1-(2,6-dichloro-4nitrophenyl)-pyrazole.

A mixture of 1-(2,6-dichloro-4-nitrophenyl)pyrazole (0.4 g, 1.55 mmol), hydrated stannous chloride (1.4 g, 6.20 mmol) and 10% hydrochloric acid (2 ml) in 17 ml of methanol is heated to 65° and stirred at this temperature for 1 hour. The mixture is poured into ice water/ether, and is then basified with 10% sodium hydroxide. Layers are separated and the aqueous layer is extracted with ethyl acetate. The combined organic layers are washed with brine and dried to give 3,5-dichloro-4-(1-pyrazolyl-aniline.

EXAMPLE 10

3,5-Dichloro-4-[3-(4-chlorophenyl)-1-pyrazolyl]aniline

A solution of 3-(4-chlorophenyl)-1-(2,6-dichloro-4-nitrophenyl)-pyrazole (0.69 g, 1.87 mmol), prepared following the procedure of Example 9, in THF/ethanol (1:4; 35 ml) is treated with platinum dioxide (43 mg) and stirred under $H_2$ at atmospheric pressure for 2 hours. The reaction mixture is filtered and concentrated to give 3,5-dichloro-4-[3-(4-chlorophenyl)-1-pyrazolyl]aniline.

EXAMPLE 11

3,5-Dichloro-4-[3,5-bis(trifluoromethyl)-1-pyrazolyl]aniline 1,1,1,5,5,5-Hexafluoro-2,4-pentanedione (0.56 g, 2.70 mmol) is added to a solution of 2,6-dichloro-4-nitrophenylhydrazine (0.30 g, 2.35 mmol) in 20 ml of methanol chilled in an ice bath. The mixture is stirred overnight at RT, after which the methanol is removed in vacuo. The residue is dissolved in toluene and a catalytic amount of p-toluenesulfonic acid (pTSOH) added. The mixture is heated under reflux and stirred for 2 hours, after which it is allowed to cool to RT and the solvent is removed in vacuo. The resulting crystals are dissolved in xylene, 40 mg of pTSOH is added and the mixture is heated under reflux for 2 hours. The resulting mixture is cooled, washed with methylene chloride, concentrated in vacuo and purified by flash chromatography to give 3,5-bis(trifluoromethyl)-1-(2,6-dichloro-4-nitrophenyl)pyrazole. Following the procedure of Example 5, the nitrophenylpyrazole is reduced by treatment with platinum dioxide and hydrogen to give 3,5-dichloro-4-[3,5-bis-(trifluoromethyl)-1-pyrazolyl]aniline.

EXAMPLE 12

3,5-Diichloro-4-(4,5,6,7-tetrahydroisoindol-2-yl)-aniline

To a mixture of sodium acetate (14.0 g) in 225 ml of acetic acid heated to refluxing is first added 2,6-dichloro-4-nitroaniline (6.40 g, 30.8 mmol), followed by 1,3-dimethoxyoctahydroisobenzofuran (5.73 g, 30.8 mmol). The reaction mixture is heated under reflux for 16 hours, after which the acetic acid is stripped off by rotoevaporation and the residue is poured into ethyl acetate and water. The aqueous layer is extracted with ethyl acetate, and the combined organic layers are washed with water and with brine and dried. The residue is purified by column chromatography to give 2-(2,6-dichloro-4-nitrophenyl)-4,5,6,7-tetrahydroisoindole, which is then reduced with stannous chloride according to Example 9 procedures to give 3,5-dichloro-4-(4,5,6,7-tetrahydroisoindol-2yl)aniline.

EXAMPLE 13

3,5-Dichloro-4-(2,5-dichloro-1-pyrrolyl)aniline

Sulfuryl chloride (4,68 g, 2.80 ml, 34.7 mmol) is added dropwise to 1-(2,6-dichloro-4-nitrophenyl)pyrrole (4.46 g, 17.4 mmol), prepared from 2,6-dichloro-4-nitroaniline and 2,5-dimethoxytetrahydrofuran following Example 12 procedures, in 20 ml of ether at 0°. After addition is completed, the mixture is stirred at RT for 60 hours. The reaction mixture is then poured into saturated aqueous sodium bicarbonate and extracted with ether. The combined organic layers are washed with brine, dried and stripped of solvent. The residue is purified by prep. TLC to give 2,5-dichloro-1-(2,6-dichloro-4-nitrophenyl)pyrrole, which is reduced with 16% aq. titanium(III) chloride to give 3,5-dichloro-4-(2,5-dichloro-1-pyrrolyl)aniline.

EXAMPLE 14

1-(2,6-dichloro-4-nitrophenyl)-5-(4-bromophenyl)-pyrazole

A solution of 2,6-dichloro-4-nitrophenol (5.0 g, 24.0 mmol) in 10 ml of tetrahydrofuran is added dropwise to a suspension of sodium hydride (1.33 g, 50% NaH, 27.6 mmol) in 20 ml of THF. After the addition, stirring is continued for 1 hour at RT and is the mixture is then added dropwise to a solution of phosgene (14.0 g) in 50 ml of methylene chloride at −10°. The mixture is allowed to warm to RT and is purged with $N_2$ to remove excess phosgene. The solvent is stripped and the residue is taken into methylene chloride. The precipitated sodium chloride is filtered and the filtrate is concentrated to give 2,6-dichloro-4-nitrophenyl chloroformate.

A mixture of the above chloroformate (1.3 g, 4.8 mmol) and 3-(4-bromophenyl)pyrazole (1.07 g, 4.8 mmol) in 30 ml of carbon tetrachloride is heated under reflux for 15 hours. The solvent is removed to give 3-(4-bromophenyl)-1-(2,6-dichloro-4-nitrophenoxycarbonyl)pyrazole.

The above (nitrophenoxycarbonyl)pyrazole (2.03 g) is heated, neat, to 210° for 3 hours. The resulting crude product is purified to give 1-(2,6-dichloro-4-nitrophenyl)-5-(4-bromophenyl)pyrazole.

EXAMPLE 15

4,5-Dichloro-3-trifluoromethylpyrazole

A solution of 5-chloro-3-trifluoromethylpyrazole (190.0 g, 1.11 mol) in 400 ml of methanol is treated with liquid bleach (5.25% NaOCl) for 3 hr. The reaction mixture is then extracted with ether, the combined ether extracts are acidified with HCl (300 ml), washed with brine, dried and concentrated to give 4,5-dichloro-3-trifluoromethylpyrazole, a light yellow solid, m.p. 58°–60°.

EXAMPLE 16

3,4,5-Trichloropyrazole

To a solution of hexachloropropene (50.0 g, 200.0 mmol) in 120 ml of THF, chilled in an ice bath, is added hydrazine monohydrate (50.0 g, 1000.0 mmol) over 10 min. The mixture is allowed to warm to RT, with rapid stirring, over 1 hr. Stirring is continued for 6 hr., after which the reaction mixture is partitioned between hexane and 10% aqueous HCl and stirred for another 4 hr. The phases are separated and the organic phase is washed with water and with brine. Acetone (50 ml) and conc. HCl (10 drops) are added, and after 2 hr. the resulting mixture is washed with brine and concentrated. Additional acetone/hexane (50 ml, 1:6) and a catalytic amount of conc. HCl are added, and after 1 hr. the mixture is concentrated, taken up in 120 ml of toluene, treated with trifluoroacetic acid (0.3 ml) and heated to reflux for 12 hr. 6N HCl (30 ml) is charged and heating is continued for 10 hr. The reaction mixture is then cooled to RT and ether and water are added. The layers are separated and the organic layer is washed with water and extracted with 5% KOH. The combined basic extracts are washed with ether, cooled and acidified with conc. HCl. This mixture is extracted with ether/hexane (2:1), and the organic extract is washed with water, dried, filtered and concentrated to give 3,4,5-trichloropyrazole, m.p. 146°–147°.

What is claimed is:

1. A compound of the following formula (A):

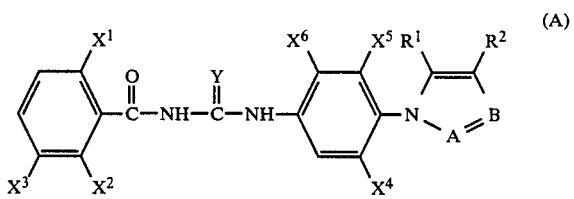

wherein,
each of $X^1$, $X^2$, $X^3$ and $X^5$ is independently hydrogen, halogen, $C_{1-8}$alkyl or $C_{1-8}$alkoxy;

$X^4$ is hydrogen, halogen, unsubstituted or halogenated $C_{1-8}$alkyl or COOR;

$X^6$ is hydrogen, halogen, $C_{1-8}$alkyl or COOR';

Y is oxygen or sulfur;

A is nitrogen or C—$R^4$;

B is nitrogen or C—$R^3$;

each of $R^1$ and $R^4$ is independently hydrogen; halogen; halogenated $C_{1-8}$alkyl; unsubstituted or halogenated $C_{1-8}$alkoxy; unsubstituted or halogenated $C_{1-8}$alkylthio; or Q, Q—O— or Q—S—, unsubstituted or substituted with 1 to 4 halogen atoms or with a $C_{1-4}$alkyl, $C_{1-4}$ alkoxy or trifluoromethyl group and 0 to 3 halogen atoms;

Q is an aromatic ring system; consisting of phenyl, pyridyl, thienyl and napthyl and each of $R^2$ and $R^3$ is independently hydrogen; halogen; cyano; unsubstituted or halogenated $C_{1-8}$alkyl; unsubstituted or halogenated $C_{1-8}$alkoxy; unsubstituted or halogenated $C_{1-8}$alkylthio; COOR''; Q, Q—O— or Q—S—, unsubstituted or substituted with 1 to 4 halogen atoms or with a $C_{1-4}$alkyl, $C_{1-4}$alkoxy or trifluoromethyl group and 0 to 3 halogen atoms; or either $R^1$ and $R^2$ or $R^2$ and $R^3$ can together form a bridging group of 4 carbon atoms, saturated or unsaturated, and unsubstituted or substituted by substituents selected from a group consisting of 1 to 4 halogen atoms or with a trifluoromethyl group and 0 to 3 halogen atoms;

each of R, $R^1$, and R'' is hydrogen or $C_{1-8}$ alkyl with the proviso that where A is C—$R^4$ and B is C—$R^3$, not all of $R^1$, $R^2$, $R^3$ and $R^4$ may be hydrogen;

and the agriculturally acceptable salts or metal complexes thereof.

2. A compound according to claim 1 wherein $X^1$ is chloro or fluoro; each of $X^2$ and $X^3$ is independently hydrogen or fluoro; $X^4$ is hydrogen, chloro, bromo, methyl or trifluoromethyl; $X^5$ is hydrogen, chloro or methyl; and $X^6$ is hydrogen, chloro or fluoro.

3. A compound according to claim 2 wherein $X^6$ is hydrogen or fluoro.

4. A compound according to claim 3 wherein A is nitrogen and B is C—$R^3$.

5. A compound according to claim 4 wherein each of $R^1$, $R^2$ and $R^3$ is independently hydrogen, bromo, chloro, fluoro or trifluoromethyl; with the proviso that not all of $R^1$, $R^2$ and $R^3$ may be hydrogen; or one of $R^1$, $R^2$ or $R^3$ is Q unsubstituted or substituted by substituents selected from a group consisting of 1 to 4 halogen atoms or with a methyl, methoxyl or trifluoromethyl group and 0 to 3 halogen atoms, and each of the remaining $R^1$, $R^2$ and $R^3$ is independently hydrogen, chloro or bromo; or $R^1$ is hydrogen, bromo, chloro or trifluoromethyl and $R^2$ and $R^3$ together form a bridging group of the formula CH=CH—CH=CH.

6. A compound according to claim 5 wherein $X^4$ is chloro, methyl or trifluoromethyl; $X^5$ is hydrogen, chloro or methyl; Y is oxygen; and Q is 4-chlorophenyl, 4-bromophenyl, 4-fluorophenyl, 4-methylphenyl, 2,4-dichlorophenyl, 3,4-dichlorophenyl, 3,5-dichlorophenyl or 4-trifluoromethylphenyl.

7. A compound according to claim 6 wherein each of $X^1$ and $X^2$ is fluoro, $X^3$ is hydrogen and $X^6$ is hydrogen or fluoro.

8. A compound according to claim 7 selected from the group consisting of N-3,5-dichloro-4-[4-chloro-3-(4-chlorophenyl)-1-pyrazolyl]phenyl-N'-2,6-difluorobenzoylurea; N-3,5-dimethyl-4-[4-chloro-3-(4-chlorophenyl)-1-pyrozolyl]phenyl-N'-2,6-difluorobenzoylurea; and N-3-chloro-4-(5-chloro-3-trifluoromethyl-1-pyrazolyl)phenyl-N'-2,6-difluorobenzoylurea.

9. A compound according to claim 6 wherein X' is chloro or fluoro, each of $X^2$ and $X^3$ is hydrogen, and $X^6$ is hydrogen or fluoro.

10. A compound according to claim 9 selected from the group consisting of N-3,5-dichloro-4-(4-bromo-1-pyrazolyl)phenyl-N'-2-chlorobenzoylurea; N-3,5-dichloro-4-(3,4-dibrom-1-pyrazolyl)phenyl-N'-2-chlorobenzoylurea; N-3,5-dichloro-4-(4,5-dichloro-3-trifluoromethyl-1-pyrazolyl)phenyl-N'-2-chlorobenzoylurea; N-3,5-dichloro-4-(3,4,5-trichloro-1-pyrazolyl)phenyl-N'-2-chlorobenzoylurea; N-3,5-dichloro-4-[3-(4-chlorophenyl)-1-pyrazolyl]-phenyl-N'-2-chlorobenzoylurea; N-3,5-dichloro-4(4,5-dichloro-3-trifluoromethyl-1-pyrazolyl)phenyl-N'-2-fluorobenzoylurea; and N-3,5-dichloro-4[3-(4-bromophenyl)-1-pyrazolyl]phenyl-N'-2-fluorobenzoylurea.

11. A compound according to claim 3 wherein A is C—$R^4$, B is C—$R^3$, and each of $R^1$ and $R^4$ is independently hydrogen or chloro.

12. A compound according to claim 11 wherein each of $R^2$ and $R^3$ is independently hydrogen, chloro, bromo or trifluoromethyl with the proviso that both $R^2$ and $R^3$ cannot be hydrogen; or one of $R^2$ or $R^3$ is Q unsubstituted or substituted by substituents selected from a group consisting of 1 to 4 halogen atoms or with a methyl, methoxy or trifluoromethyl group and 0 to 3 halogen atoms, and the other of $R^2$ or $R^3$ is hydrogen, chloro or bromo; or $R^2$ and $R^3$ together form a bridging group of the formula $CH_2$—$Ch_2$—$Ch_2$—$Ch_2$.

13. A compound according to claim 12 wherein Y is oxygen; $X^4$ is chloro or trifluoromethyl; and Q is 4-chlorophenyl, 2,4-dichlorophenyl, 3,4-dichlorophenyl, 3,5-dichlorophenyl or 4-trifluoromethylphenyl.

14. A compound according to claim 13 wherein each of $R^1$ and $R^4$ is hydrogen, each of $X^3$ and $X^6$ is hydrogen and each of $X^4$ and $X^5$ is chloro.

15. A compound according to claim 14 wherein each of $X^1$ and $X^2$ is fluoro.

16. The compound N-3,5-dichloro-4(3,4-dichloro-1-pyrrolylphenyl-N'-2,6-difluorobenzoylurea, according to claim 15.

17. A compound according to claim 14 wherein $X^1$ is chloro and $X^2$ is hydrogen.

18. A method for the control of pests which comprises applying to the pest or its locus in a pest-controlling amount a compound of formula A as defined in claim 1.

19. A pesticidal composition comprising a pesticidally effective amount of a compound according to claim 1 together with an agriculturally acceptable diluent or carrier.

* * * * *